US008505536B2

(12) United States Patent
Kielow et al.

(10) Patent No.: US 8,505,536 B2
(45) Date of Patent: Aug. 13, 2013

(54) RESPIRATORY HALF-MASK

(75) Inventors: Detlef Kielow, Berlin (DE); Michael Horn, Berlin (DE); Klaus Schmidtke, Berlin (DE)

(73) Assignee: MSA Auer GmbH, Berlin (DE)

( * ) Notice: Subject to any disclaimer, the term of this patent is extended or adjusted under 35 U.S.C. 154(b) by 672 days.

(21) Appl. No.: 12/742,704

(22) PCT Filed: Oct. 1, 2008

(86) PCT No.: PCT/EP2008/063172
§ 371 (c)(1),
(2), (4) Date: May 13, 2010

(87) PCT Pub. No.: WO2009/062784
PCT Pub. Date: May 22, 2009

(65) Prior Publication Data
US 2010/0263673 A1 Oct. 21, 2010

(30) Foreign Application Priority Data
Nov. 16, 2007 (DE) ........................ 10 2007 055 238

(51) Int. Cl.
*A61M 11/00* (2006.01)

(52) U.S. Cl.
USPC ............ 128/205.25; 128/206.27; 128/206.28

(58) Field of Classification Search
USPC ............ 128/206.27, 206.28, 207.11, 205.25, 128/205.27, 206.15, 206.16, 206.17
See application file for complete search history.

(56) References Cited

U.S. PATENT DOCUMENTS

| | | | | | |
|---|---|---|---|---|---|
| 2,942,602 | A | | 6/1960 | Seeler | |
| 3,079,917 | A | * | 3/1963 | Pate | 128/206.27 |
| 3,092,105 | A | * | 6/1963 | Gabb | 128/206.27 |
| 3,234,940 | A | * | 2/1966 | Morton, Jr. | 128/206.27 |
| 3,347,229 | A | * | 10/1967 | Heitman | 128/201.19 |
| 4,960,121 | A | | 10/1990 | Nelson | |
| 5,690,102 | A | * | 11/1997 | Bertheau et al. | 128/207.11 |
| 6,062,221 | A | * | 5/2000 | Brostrom et al. | 128/206.27 |
| 6,457,473 | B1 | * | 10/2002 | Brostrom et al. | 128/207.11 |

(Continued)

FOREIGN PATENT DOCUMENTS

| | | | |
|---|---|---|---|
| EP | 0808641 | A1 | 11/1997 |
| EP | 1019151 | A1 | 4/1999 |
| WO | 03033077 | A1 | 4/2003 |
| WO | WO-03/033077 | A | 4/2003 |

OTHER PUBLICATIONS

International Preliminary Report on Patentability for PCT/EP2008/063172, issued Jun. 1, 2010.

(Continued)

*Primary Examiner* — Steven Douglas
(74) *Attorney, Agent, or Firm* — The Webb Law Firm

(57) ABSTRACT

A respiratory half-mask, including a mask body having a front or side filters, and exhalation valves, a head support with two side straps emanating from support, and a strap guide part fastened on the mask body for sliding the mask body along the side straps from a usage position for covering a mouth and a nose of the user into a position for exposing the face of the user. At least one clamping element is adjustably attached to the strap guide part for clamping the side straps to the strap guide part and for fixing the mask body on the two side straps in a usage position.

13 Claims, 6 Drawing Sheets

(56) References Cited

U.S. PATENT DOCUMENTS

| | | | | |
|---|---|---|---|---|
| 6,715,490 | B2 * | 4/2004 | Byram | 128/206.27 |
| 7,464,705 | B2 * | 12/2008 | Tanizawa et al. | 128/201.25 |
| 7,650,884 | B2 * | 1/2010 | Flannigan et al. | 128/206.12 |

OTHER PUBLICATIONS

Written Opinion of the International Searching Authority for PCT/EP2008/063172, issued Jun. 1, 2010.

* cited by examiner

A-A

RESPIRATORY HALF-MASK

BACKGROUND OF THE INVENTION

1. Field of the Invention

The invention relates to a respiratory half-mask comprising a mask body fitted with front or side filters, a head strap support with two side straps emanating from said support, which can be connected at the free ends, and a strap guide part fastened on the mask body for sliding the mask body along the side straps from a usage position covering mouth and nose into a position which exposes the face.

Respiratory half-masks are used for covering the mouth and nose of the user with a mask body which is configured with side filters or a front filter to protect the mask wearer from contaminants present in the air, and has at least one exhalation valve. The half-mask is usually held on the head of the user with the aid of a strap connected to the mask, consisting of side straps connected to a head support. The strap and its connection to the mask body should be designed such that the respiratory half-mask can be donned and doffed or adjusted simply and rapidly and can furthermore be held on the face of the mask wearer in a reliable sealing manner and with high wearing comfort, and specifically from the point of view of the heavy filter elements and a high physical stressing of the user. An important requirement with regard to the usage comfort of the respiratory half-mask consists in being able to remove the half-mask only temporarily from the mouth and nose, for example, in order to be able to reach the mouth only temporarily or because the surroundings are free from contaminants. Donning or doffing the half-mask is particularly complex if the strap is connected to a head support supported on the head of the user which is worn under a helmet which must be taken off and put on again every time the respiratory half-mask is donned or doffed.

2. Description of the Related Art

Known from EP 1 019 151 B1 is a respiratory half-mask with a strap guide part attached to the mask body in which the two side straps fastened to a head support are each guided in an upper guide and in a lower guide and are guided from the upper guide to the obliquely opposite lower guide so that they cross over each other. The four guides form an advantageous four-point holding of the mask body on the face of the user. The mask body can be moved along the side straps guided in the upper and lower guides from a position covering the mouth and nose of the user into a position located below the face or in the opposite direction. That is, the mask can be donned or doffed relatively rapidly and simply without needing to remove a protective helmet worn over the head support. However, the secure fit of the mask body and the reliable sealing on the face are limited insofar as the mask body can slip on the face as a result of the weight caused by the filters and under high physical stressing of the user, in particular in connection with moisture forming between the mask body and the face, and consequently a reliable seal is not ensured. For bracing the mask body on the face of the user, the side straps attached adjustably to the head support must be tensioned. The loose ends of the side straps hanging down from the head support, which are provided for firmly tightening the respiratory half-mask on the face of the user are perceived as interfering by the user.

A respiratory half-mask described in EP 0 808 641 B1 has a strap guide element on both outer sides for respectively one side strap connected to a head support, the free ends of which have a closure element to allow the two ends to be connected to one another behind the head. The two strap guide elements have an elongated curved slot in which the relevant side strap can run slidingly and in which it acquires the curved structure of the slot in order to enter into frictional engagement with the strap guide element but in which it can still move in a sliding manner. In this way, the half-mask can be adjusted by overcoming the frictional forces from a position abutting against the face into a position below the face which exposes the nose and mouth. The frictional forces are intended to prevent self-slippage of the half-mask from the face. Apart from the fact that only an unstable two-point holding of the half-mask on the face is ensured with the two strap guide elements, with the aid of the frictional forces on the side straps produced in the curved slot it is not possible to fix the mask body securely on the side straps, and therefore on the face, and in particular specifically not under physical stressing and corresponding vibrations. A significant increase in the frictional forces on the side straps guided in lateral strap guides, which has already been proposed, conflicts with the requirement for a simple and rapid adjustment of the half-mask in the respective position and high wear or damage to the side straps.

Known from WO 03/033077 A1 is a respiratory half-mask which likewise allows a rapid adjustment from a position sealingly covering the mouth and nose into a hanging-down position exposing the face. Detachably attached to the mask body is a strap guide element to which respectively one adjustable-length neck strap is fastened at two lower connecting points, the free ends whereof being connectable to one another behind the neck of the user. Two side straps connected to a head support and running in lateral guides are fastened at the lower edge of a locking flap which is connected pivotally to the strap guide element on the opposite edge. In the downward-pivoted locked position on the mask body, the mask body abuts against the face of the user. However, the side straps can also be re-tensioned on the head support. The two neck straps are connected to one another behind the neck and can also be re-tensioned. By pivoting the locking flap upwards, the length of the side straps is extended so that the respiratory half-mask can be removed from the face or, when the neck straps are released, held hanging on the head support below the face. This respiratory half-mask is disadvantageous insofar as neck straps must be provided along with the side straps and these must be braced in each case when donning the mask. In addition, the locking flap can easily work loose so that respiratory protection is not reliably ensured.

SUMMARY OF THE INVENTION

It is the object of the invention to configure a respiratory half-mask of the type mentioned initially so as to ensure simple, rapid donning and doffing of the mask, high usage comfort and reliable respiratory protection.

According to the invention, the object is achieved with a respiratory half-mask configured according to the features of patent claim 1. Further features and advantageous further developments of the invention are obtained from the dependent claims.

The basic idea of the invention consists in that in a respiratory half-mask having a strap guide part attached to the mask body, which is provided for adjusting the mask body along the side straps, a movable or adjustable clamping element is attached to the strap guide part in order to clamp the side straps by actuating the clamping element in the mouth and nose covering position of the mask body on the strap guide part and thereby fix the mask body in the usage position. Despite a high weight caused by the filter body or bodies and high physical stressing of the mask wearer, the half-mask cannot unintentionally slip or be unintentionally moved into a position in which the respiratory protection of the user is no longer ensured. Only after releasing the clamping element and releasing the connecting elements at the ends of the side straps projecting downwards from the strap guide part can the mask body connected to the strap guide part be displaced along the side straps into a readiness position away from the face if respiratory protection is temporarily not required.

If required, the mask body with the strap guide part can be displaced rapidly back into the usage position and fixed with the clamping elements again on the side straps so that the mask body abuts firmly on the face. The ends of the side straps projecting downwards from the strap guide part are then connected to one another behind the neck of the user so that the half-mask is reliably held sealingly on the face of the user at four connecting points, i.e. two upper strap entry locations and two lower strap exit locations of the two side straps—forming a single strap loop—on the strap guide part.

According to a further feature of the invention, strap friction webs are formed in the strap guide part by which means the strap guide part can be fixed in a position on the side straps corresponding to the usage position of the mask body. In such a preliminary adjustment achieved by placing the side straps onto the strap friction webs, which in certain cases can be required to protect the user, the respiratory half-mask is deliberately prevented from being displaced into a position away from the face despite the released clamping element.

In a further embodiment of the invention, the strap guide part comprises two upper strap guide channels running from its outer sides to the middle and two lower strap guide channels running obliquely downwards preferably at an acute angle to these. The strap guidance between the successive strap guide channels formed respectively outside and inside on the strap guide part is accomplished by means of a strap deflecting edge on which the clamping element can act and fix the strap guide part with the mask body on the side straps.

The upper strap guide channels running on the outer surface of the strap guide part each have a guide slot at the outer end opposite the strap deflecting edge which defines the upper connecting point of the respective side strap whilst the lower connecting points are formed by the strap exit opening from the lower strap guide channels running on the inside. The lower strap guide channels running on the inside are in each case delimited by a cover plate formed by the strap guide part and a fastening cylinder moulded onto the strap guide part.

The two strap deflecting edges are preferably arranged oppositely at a distance and form a clamping opening into which a single clamping element can be moved in order to clamp both side straps simultaneously on the respective strap deflecting edge.

In one embodiment of the invention, the clamping element is a clamping lever pivotally mounted on the strap guide part which is matched in length and width to the size of the clamping opening. Clamping grooves are formed in the opposite longitudinal sides of the clamping lever which, in the clamping position, grip over the side strap guided around the rounded strap deflecting edge and effect a locking of the clamping lever and a secure clamping of the side straps.

In a further embodiment of the invention, the clamping lever is configured as a plate which is pivotable about an axis of rotation, the clamping grooves being formed in the side edge surfaces thereof and a handle for actuating the clamping lever being formed on the upper side thereof.

In a further embodiment of the invention, the above-mentioned fastening cylinder connected integrally to the strap guide part and serving as a strap guide element is provided with latching elements and can be placed on a connecting cylinder attached to the mask body and locked with this. When the connecting cylinder surrounds an exhalation valve integrated in the mask body, the outwardly pointing open side of the fastening cylinder is covered with a protective grid. However, the connecting cylinder can also be configured for the fastening of a front filter. In this case, the protective grid is obviously omitted.

In a further embodiment of the invention, two gripping recesses disposed at a distance from one another are formed in the outer surface of the strap guide part which allow easy handling of the respiratory half-mask when putting on or removing from the face.

BRIEF DESCRIPTION OF THE DRAWINGS

An exemplary embodiment of the invention is explained in detail with reference to the drawings. In the figures.

DETAILED DESCRIPTION OF THE PREFERRED EMBODIMENTS

The respiratory half-mask comprises a mask body 1 which covers the face of a user in the region of the mouth and the nose, a strap guide part 2 detachably fastened to the mask body 1 and a strap consisting of a head support 3 and two side straps 4 fastened thereto for holding the respiratory half-mask in a usage position on the face or in a pulled-down or downward-hanging readiness position (drop-down position) below the face. In the case last described, the mask, without removing the protective helmet, is certainly far from the face but can be rapidly donned again when required.

Figure 1:
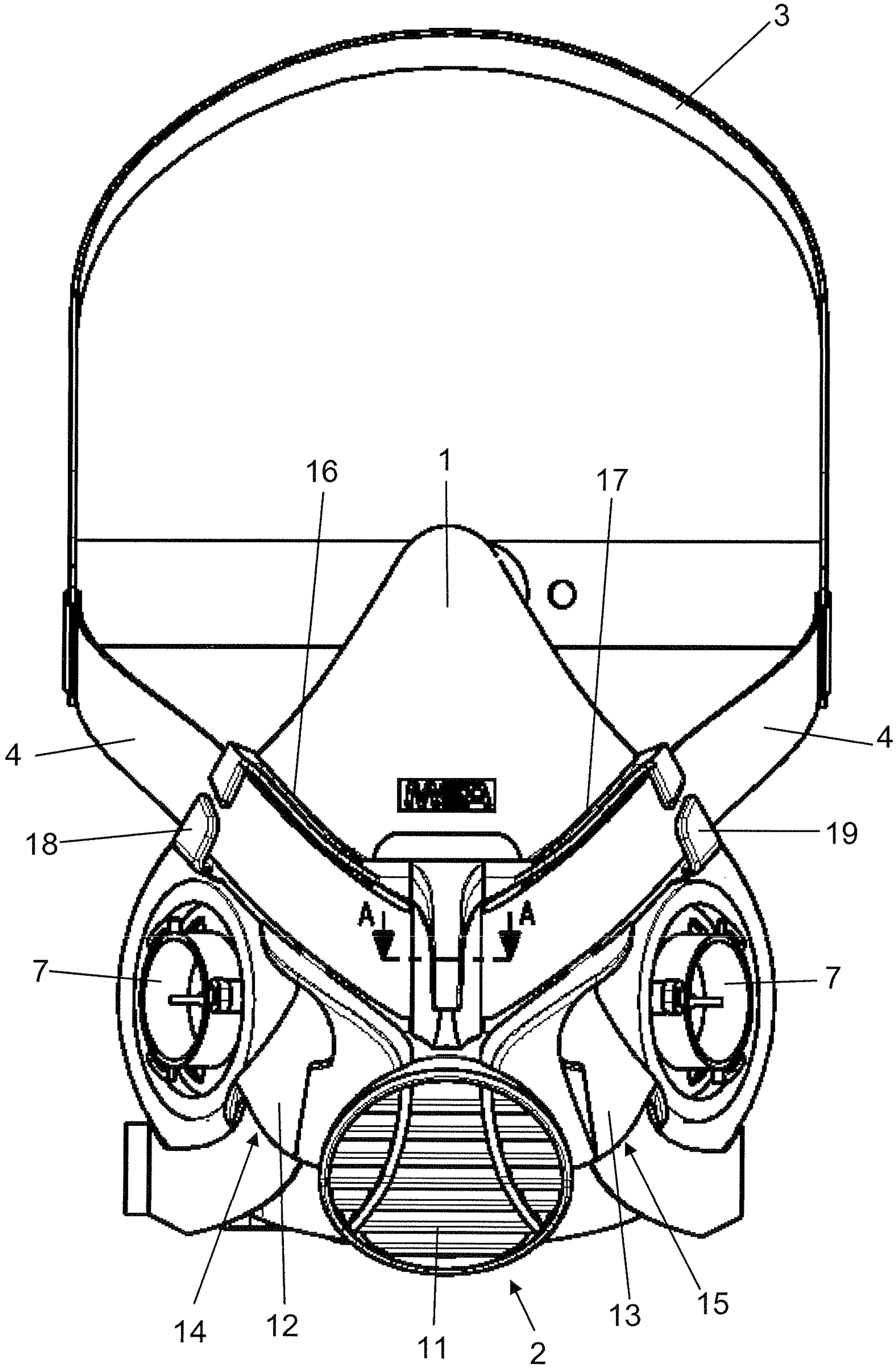
FIG. 1 shows a perspective front view of a respiratory half-mask with a strap guide part comprising a clamping element, attached detachably to the mask body.
Figure 2:
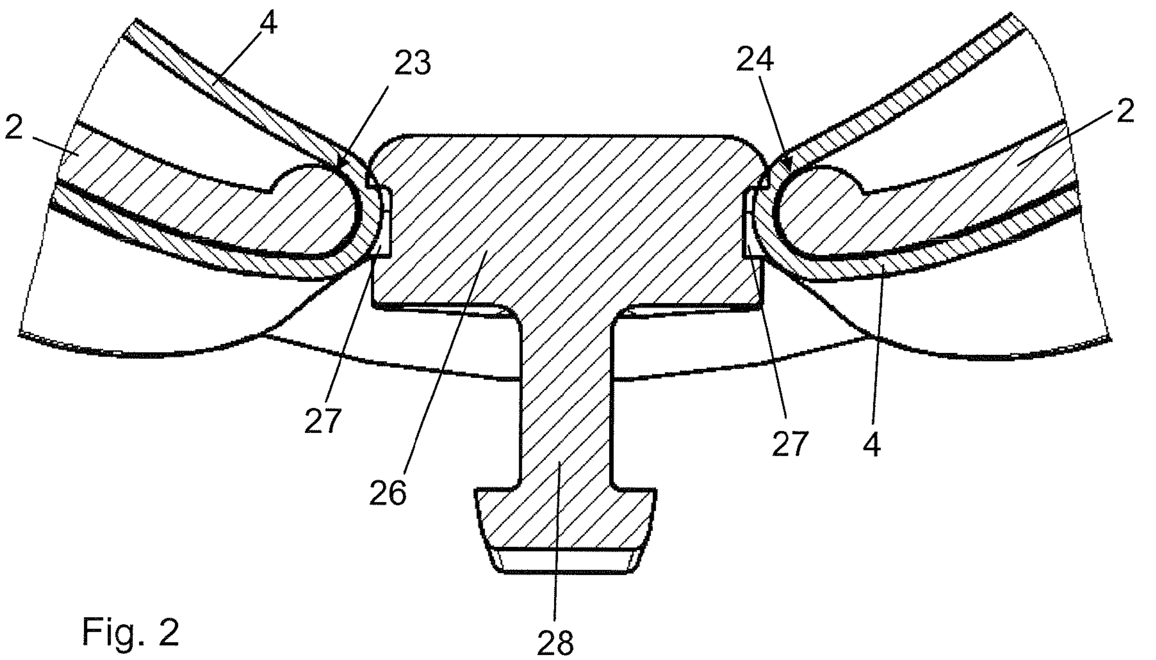
FIG. 2 shows a sectional view of the clamping arrangement according to the line A-A in FIG. 1.
Figure 3:
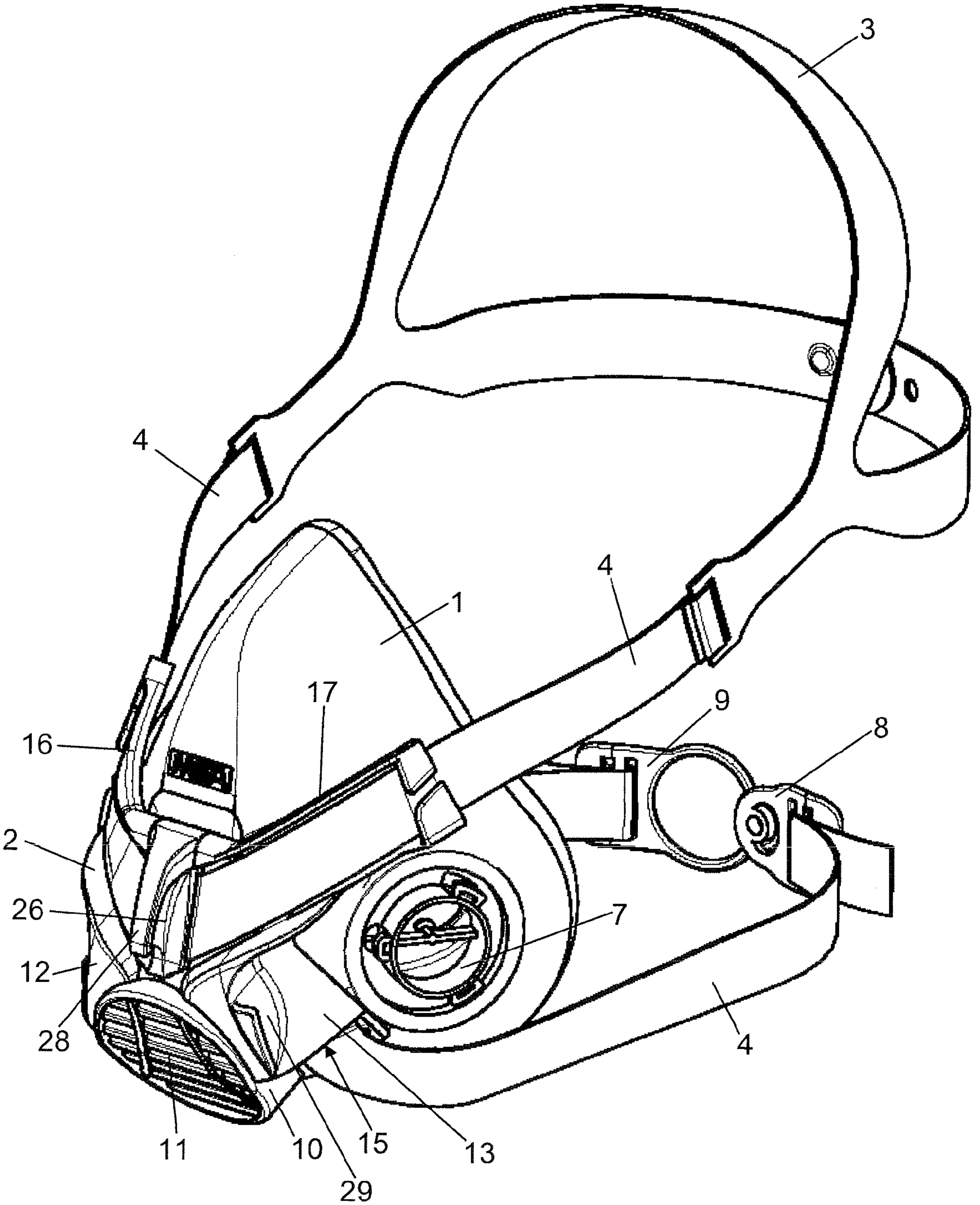
FIG. 3 shows a perspective side view of the respiratory mask in a state provided for use with side straps firmly clamped and connected at the free ends.
Figure 4:
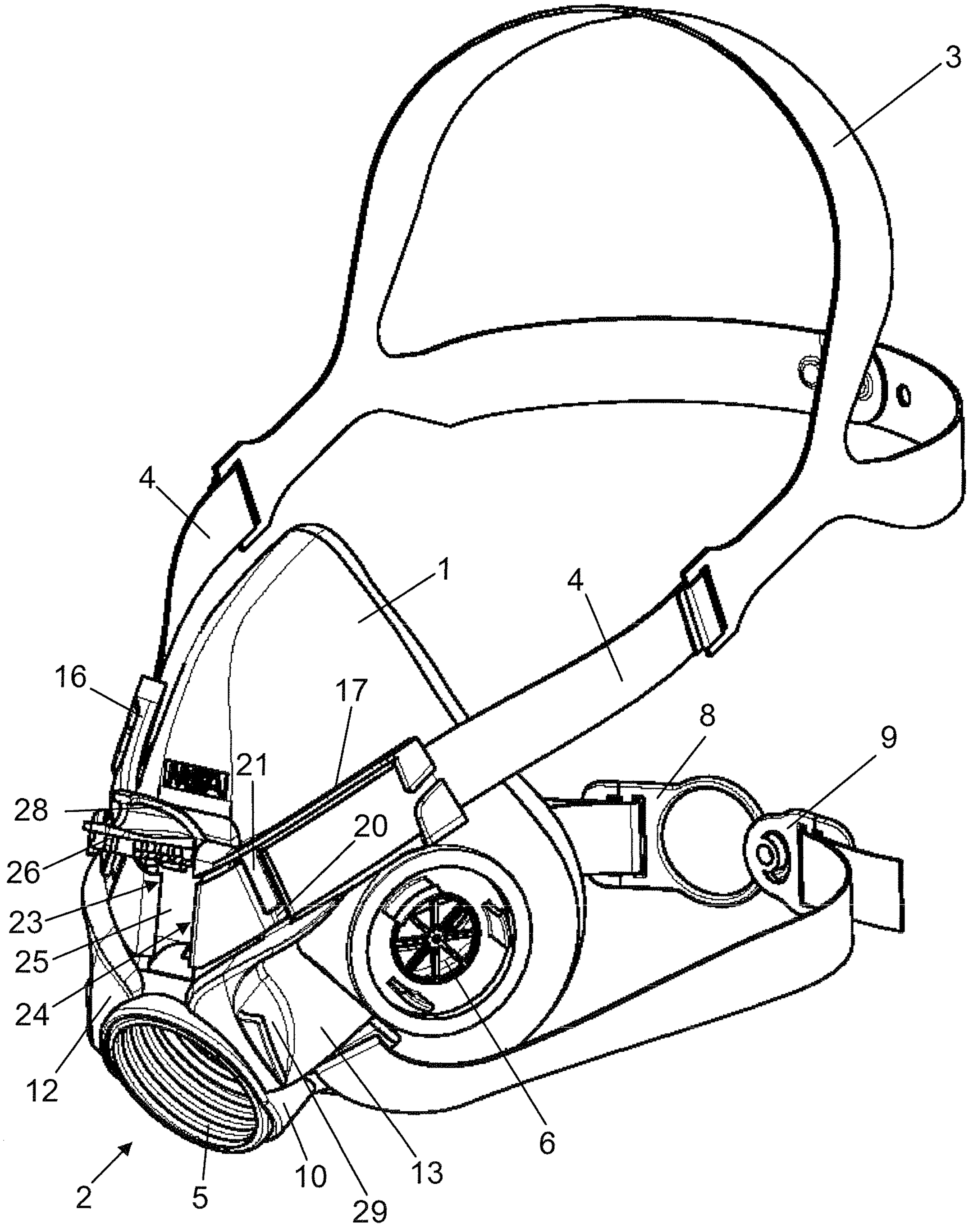
FIG. 4 shows a perspective side view of the respiratory mask with opened clamping element in a state which cannot be pulled down from the face.
Figure 5:
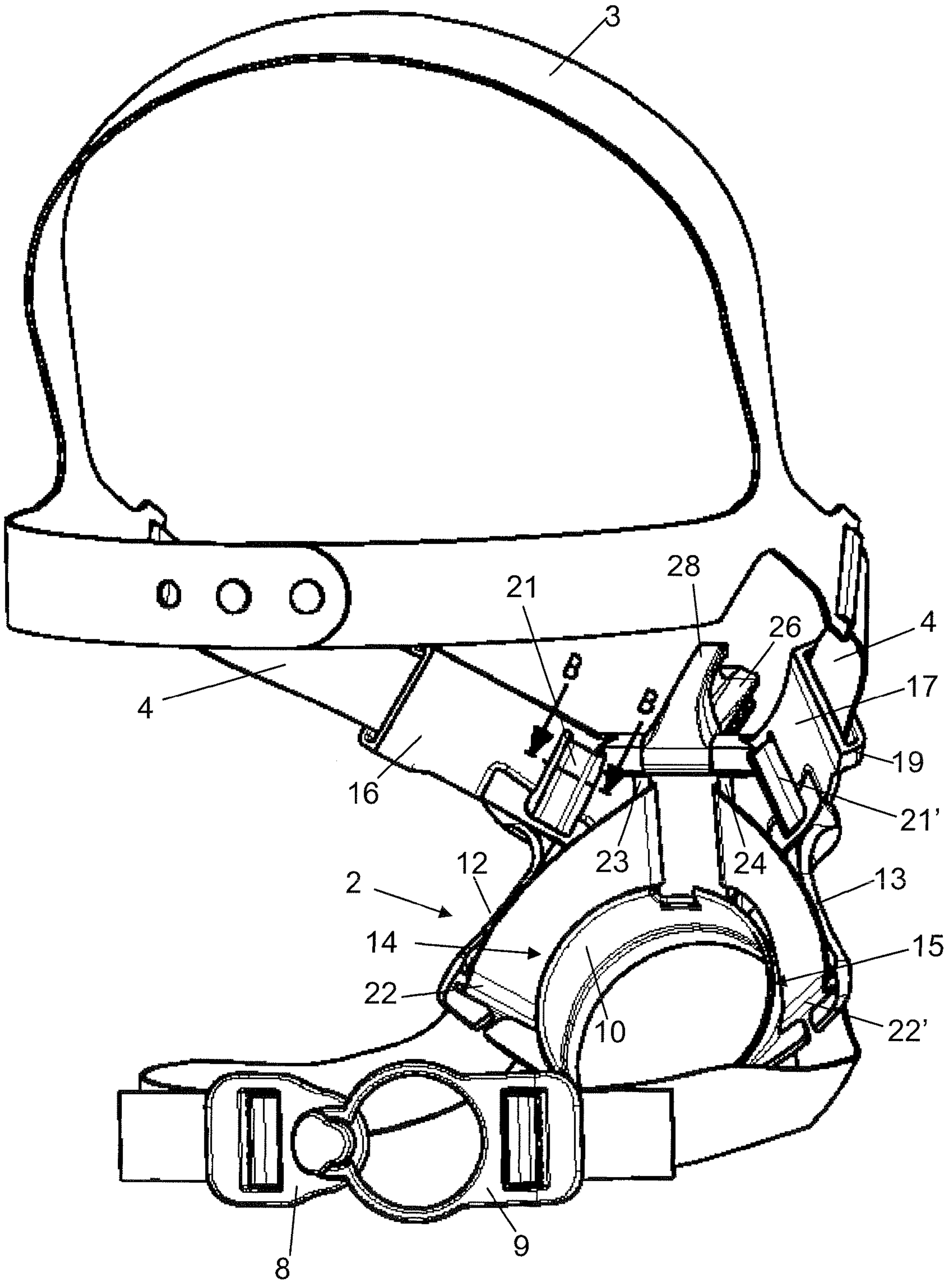
FIG. 5 shows a rear view of the strap guide part for the side straps with the clamping element opened according to FIG. 4.
Figure 6:
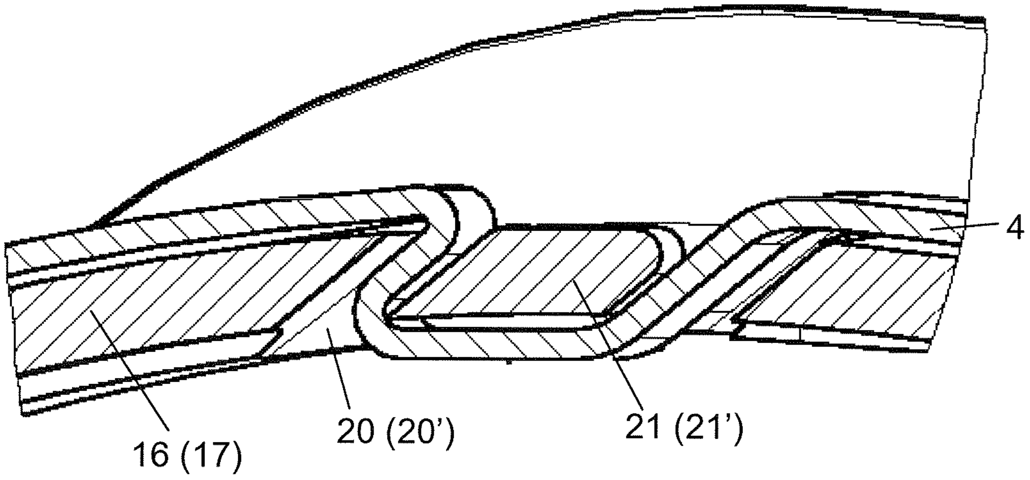
FIG. 6 shows a sectional view along the line B-B in FIG. 5.

As can be seen in FIG. 4, a connecting cylinder 5 is provided on the mask body 1 which, only according to the embodiment shown in FIG. 4, is used for the detachable fastening of a respiratory protection front filter (not shown). In this version, shown in FIG. 4, two lateral exhalation valve seats 6 are integrated in the mask body 1. In the respiratory half-masks with two lateral filter connections 7 shown in FIGS. 1 and 3, the connecting cylinder surrounding an exhalation valve (not shown) formed centrally in the mask body 1 cannot be identified. Connecting means 8, 9 are attached to the free ends of the side straps 4 in order to be able to connect the elastic side straps 4 which can be adjusted to the desired length, to form a single loop behind the head or neck of the user.

The two side straps 4 are guided in the strap guide part 2 attached to the mask body 1 for donning and doffing the mask or are held in the usage position. The strap guide part 2 is fastened by means of a fastening cylinder 10 formed integrally thereon, which can be plugged onto the connecting cylinder 5 on the mask body 1 and can be locked on this by means of moulded-on latching means (FIG. 4). In the case of the embodiment according to FIGS. 1 and 3 in which the connecting cylinder (not shown) surrounds an exhalation valve (not shown) formed centrally in the mask body 1, the fastening cylinder 10 is covered with a protective grid 11 on the air outlet side pointing away from the mask body 1.

Two cover plates 12, 13 of the strap guide part 2 formed on the left and right side at a distance from the circumferential surface of the fastening cylinder 10 each form an inner lower, left and right, strap guide channel 14, 15 respectively with the remotely opposite outer surface of the fastening cylinder 10. At the top the cover plates 12, 13 are each adjoined by an upper, left and right, strap guide channel 16, 17 located on the outer surface of the strap guide part with a guide slot 18, 19 formed at the end thereof. In the upper strap guide channel 16, 17, respectively one slot opening 20, 20' with a first strap friction web 21, 21' disposed therein is formed in the strap guide surface thereof. A second strap friction web 22, 22' adjoins the lower strap guide channel 14, 15 in each case.

The transition between the upper outer strap guide channel 16 or 17 and the lower inner strap guide channel 14 or 15 supporting this at an angle in each case, is formed by two remotely parallel opposite rounded strap deflecting edges 23, 24 which define the clamping opening 25. Located at the clamping opening 25 is an adjustable clamping element 26, here in the form of a pivotable clamping lever having two lateral clamping grooves 27 and a handle 28. Gripping recesses 29 are formed on the outer surface on the strap guide part 2, which allow easy handling of the respiratory half-mask.

The function of the previously described strap guide part 2 is explained hereinafter:

The strap guide part 2 with its fastening cylinder 10 is plugged onto the connecting cylinder 5 provided on the mask body 1 and locks detachably thereon. The upper ends of the side straps 4 are firmly connected to the head support 3. No hanging-down strap ends which impede the user are provided for adjusting the strap tension. The side straps 4 are guided via the guide slot 18 or 19, the upper outer strap guide channel 16 or 17, the strap deflecting edge 23 or 24 and the lower inner strap guide channel 14 or 15 in the strap guide part 2. After displacing the respiratory half-mask along the side straps 4 into a position covering the mouth and the nose, the respiratory half-mask is fixed on the side straps 4, by firmly clamping the side straps 4 at the strap deflecting edges 23, 24 with the aid of the clamping element 26. At this point the mask body 1 is already relatively close to the face of the user. The connecting means 8, 9 are then connected to one another behind the neck of the user and the strap ends pulled tight. The respiratory half-mask is now held at four connecting points on the face. As a result of the firm clamping of the side straps 4 at the strap deflecting edges 23, 24 created between the upper and lower strap guide channel, the mask cannot shift by itself even under high filter weight, strong physical stressing, impacts on the respiratory half-mask or formation of perspiration on the face so that the respiratory protective function of the mask is ensured at all times. The clamping element 26 can be locked at the strap deflecting edges 23, 24 by means of its clamping grooves 27 so that the side straps 4 are securely clamped and the clamping element 26 cannot be released unintentionally. On the other hand, after releasing the clamping element 26 the respiratory half-mask can be displaced easily and rapidly into a position held below the face or, after releasing the connecting means 8, 9, a hanging position.

In certain cases it may be necessary to deny the mask carrier an intermediate displacement of the respiratory half-mask from the face. For this purpose, the above-mentioned first and second strap friction webs 21, 21' and 22, 22' are formed on the strap guide channels 14, 15 and 16, 17 and the side straps 4 can be placed around these so that the side straps are fixed as a result of the frictional connection between the side strap and the friction web(s) formed pointedly or at an angle on the strap guide part 2 and the mask itself cannot be removed from the face even when the clamping element 26 is released (non drop-down position).

REFERENCE LIST

1 Mask body
2 Strap guide part
3 Head support
4 Side straps
5 Connecting cylinder
6 Lateral exhalation valve seat
7 Lateral filter connection
8, 9 Connecting means
10 Fastening cylinder
11 Protective grid
12, 13 Cover plate
14, 15 Lower inner strap guide channels
16, 17 Upper outer strap guide channels
18, 19 Guide slots
20, 20' Slot opening
21, 21' Upper strap friction web
22, 22' Lower strap friction web
23, 24 Strap deflecting edge
25 Clamping opening
26 Clamping element
27 Clamping grooves
28 Handle
29 Gripping recess

The invention claimed is:

1. A respiratory half-mask comprising a mask body having at least one of front and side filters, and exhalation valves, a head support with two side straps emanating from said support, and a strap guide part fastened on the mask body for sliding the mask body along the side straps from a usage position configured to cover a mouth and nose of a user into a position configured to expose a face of the user, wherein at least one clamping element is adjustably attached to the strap guide part for clamping the side straps to the strap guide part and for fixing the mask body on the two side straps in the usage position.

2. The respiratory half-mask according to claim 1, wherein the two side straps are each guided in an upper strap guide channel formed on the strap guide part and, after deflection, at a rounded strap deflecting edge in a lower strap guide channel, wherein the clamping element acts on the strap deflecting edges covered by a side strap section.

3. The respiratory half-mask according to claim 2, wherein the two strap deflecting edges are disposed oppositely at a distance and define a clamping opening into which a common clamping element can be moved, which clamps both side straps simultaneously at the respective strap deflecting edge.

4. The respiratory half-mask according to claim 3, wherein the common clamping element is a pivotally fastened clamping lever associated with a clamping opening with opposing clamping grooves matched in size and distance to the strap deflecting edges, which, in the clamping state, partially embrace the respective strap deflecting edge with the deflected side strap section, and lock the clamping lever in the clamping position.

5. The respiratory half-mask according to claim 4, wherein the clamping lever is a plate mounted pivotally about an axis at an upper edge of the clamping opening and has a handle, and in which the clamping grooves are formed in an opposite side surfaces of the plate.

6. The respiratory half-mask according to claim 2, wherein the upper strap guide channels on the mask body run laterally from the strap deflecting edges outwards, and the lower strap guide channels run laterally obliquely downwards at an angle of <90.degree. to the respective upper strap guide channel.

7. The respiratory half-mask according to claim 2, wherein the upper strap guide channels are formed on an outer surface of the strap guide part and at an end opposite the strap deflecting edge, each having a guide slot defining upper connecting points of the side straps and the lower strap guide channels run on the inner side of the strap guide part, wherein strap outlet openings form lower connecting points of the side straps on the mask.

8. The respiratory half-mask according to claim 7, wherein the lower strap guide channels are formed by a fastening cylinder and cover plates of the strap guide part running at a distance from an outer surface thereof.

9. The respiratory half-mask according to claim 8, wherein the fastening cylinder connected integrally to the strap guide part can be plugged onto a connecting cylinder attached to the mask body, and is held thereon by latching elements.

10. The respiratory half-mask according to claim 9, wherein the connecting cylinder is positioned around an exhalation valve disposed centrally in the mask body, and a protective grid covers the air outlet opening formed by the fastening cylinder and is integrated in the strap guide part.

11. The respiratory half-mask according to claim 9, wherein the connecting cylinder is configured for the detachable fastening of a front filter.

12. The respiratory half-mask according to claim 2, wherein upper and lower strap friction webs are associated with at least one of the upper and the lower strap guide channels for fixing the side straps in the usage position of the mask body, such that even when the clamping element is released, the mask cannot be moved into a position remote from the face.

13. The respiratory half-mask according to claim 1, wherein two gripping recesses formed at a distance from one another are provided on the outer side of the strap guide part for handling the half-mask.

* * * * *